US00PP22133P2

(12) United States Plant Patent
Saul

(10) Patent No.: US PP22,133 P2
(45) Date of Patent: Sep. 6, 2011

(54) ***ECHINACEA* PLANT NAMED 'SOLAR FLARE'**

(50) Latin Name: ***Echinacea tennesseensis*×*(Echinacea purpurea*×*Echinacea paradoxa)***
Varietal Denomination: Solar Flare

(75) Inventor: Richard Gregg Saul, Cleveland, GA (US)

(73) Assignee: ITSAUL Plants, Alpharetta, GA (US)

( * ) Notice: Subject to any disclaimer, the term of this patent is extended or adjusted under 35 U.S.C. 154(b) by 0 days.

(21) Appl. No.: 12/807,632

(22) Filed: Sep. 9, 2010

(51) Int. Cl.
*A01H 5/00* (2006.01)

(52) U.S. Cl. ..... Plt./428

(58) Field of Classification Search ..... Plt./428
See application file for complete search history.

*Primary Examiner* — Kent L Bell
(74) *Attorney, Agent, or Firm* — C. A. Whealy

(57) ABSTRACT

A new and distinct cultivar of *Echinacea* plant named 'Solar Flare', characterized by its upright and columnar plant habit; moderately vigorous growth habit; large inflorescences with red-colored ray florets; strong dark purple-colored flowering stems that hold the inflorescences upright; and good garden performance.

2 Drawing Sheets

Botanical designation: *Echinacea tennesseensis*×(*Echinacea purpurea*×*Echinacea paradoxa*).
Cultivar denomination: 'SOLAR FLARE'.

BACKGROUND OF THE INVENTION

The present invention relates to a new and distinct cultivar of *Echinacea* plant, botanically known as *Echinacea tennesseensis*×(*Echinacea purpurea*×*Echinacea paradoxa*) and hereinafter referred to by the name 'Solar Flare'.

The new *Echinacea* is a product of a planned breeding program conducted by the Inventor in Dahlonega, Ga. The objective of the breeding program is to create new hardy and vigorous *Echinacea* plants with unique and attractive ray and disc floret coloration.

The new *Echinacea* plant originated from a cross-pollination during the summer of 2007 of an unnamed selection of *Echinacea tennesseensis,* not patented, as the female, or seed, parent with *Echinacea purpurea*×*Echinacea paradoxa* 'Emily Saul', disclosed in U.S. Plant Pat. No. 18,768, as the male, or pollen, parent. The new *Echinacea* plant was discovered and selected by the Inventor as a single flowering plant from within the progeny of the stated cross-pollination grown in a controlled environment in Dahlonega, Ga. during the spring of 2008.

Asexual reproduction of the new *Echinacea* plant by tissue culture in a controlled environment in Alpharetta, Ga. since the spring of 2009 has shown that the unique features of this new *Echinacea* plant are stable and reproduced true to type in successive generations.

SUMMARY OF THE INVENTION

Plants of the new *Echinacea* have not been observed under all possible environmental conditions. The phenotype may vary somewhat with variations in environment such as temperature and light intensity, without, however, any variance in genotype.

The following traits have been repeatedly observed and are determined to be the unique characteristics of 'Solar Flare'.

These characteristics in combination distinguish 'Solar Flare' as a new and distinct cultivar of *Echinacea:*

1. Upright and columnar plant habit.
2. Moderately vigorous growth habit.
3. Large inflorescences with red-colored ray florets.
4. Strong dark purple-colored flowering stems that hold the inflorescences upright.
5. Good garden performance.

Plants of the new *Echinacea* differ from plants of the female parent selection in the following characteristics:

1. Plants of the new *Echinacea* and the female parent selection differ in peduncle color as plants of the female parent selection have green-colored peduncles.
2. Plants of the new *Echinacea* and the female parent selection differ in ray floret color as plants of the female parent selection have pink-colored ray florets.

Plants of the new *Echinacea* differ from plants of the male parent, 'Emily Saul', in the following characteristics:

1. Plants of the new *Echinacea* are taller than plants of 'Emily Saul'.
2. Plants of the new *Echinacea* and 'Emily Saul' differ in ray floret color as plants of 'Emily Saul' have dark red purple-colored ray florets.

Plants of the new *Echinacea* can be compared to plants of *Echinacea purpurea* 'Tomato Soup', disclosed in U.S. Plant Pat. No. 19,427. In side-by-side comparison plants of the new *Echinacea* differed from plants of 'Tomato Soup' in the following characteristics:

1. Plants of the new *Echinacea* were taller than plants of 'Tomato Soup'.
2. Plants of the new *Echinacea* and 'Tomato Soup' differed in ray floret color as plants of 'Tomato Soup' had bright red orange-colored ray florets.
3. Plants of the new *Echinacea* and 'Tomato Soup' differed in peduncle color as plants of 'Tomato Soup' had green-colored peduncles.

BRIEF DESCRIPTION OF THE PHOTOGRAPHS

The accompanying photographs illustrate the overall appearance of the new *Echinacea* plant. The photographs show the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet comprises a side perspective view of a typical flowering plant of 'Solar Flare' grown in a container.

The photograph on the second sheet is a close-up view of a typical flowering plant of 'Solar Flare'.

DETAILED BOTANICAL DESCRIPTION

The aforementioned photographs and following observations and measurements describe plants grown during the summer in 17-cm containers in an outdoor nursery in Alpharetta, Ga. and under conditions and practices which approximate those generally used in commercial *Echinacea* production. During the production of the plants, day temperatures averaged 29° C. and night temperatures averaged 24° C. Plants were six months old when the photographs and description were taken. In the following description, color references are made to The Royal Horticultural Society Colour Chart, 2007 Edition, except where general terms of ordinary dictionary significance are used.

Botanical classification: *Echinacea purpurea*×*Echinacea paradoxa* 'Solar Flare'.

Parentage:

*Female, or seed, parent.*—Unnamed selection of *Echinacea tennesseensis,* not patented.

*Male, or pollen, parent.*—*Echinacea purpurea*×*Echinacea paradoxa* 'Emily Saul', disclosed in U.S. Plant Pat. No. 18,768.

Propagation:

*Type.*—By tissue culture.

*Time to initiate roots.*—About three weeks at 22° C.

*Time to produce a rooted young plant, summer.*—About four weeks at 22° C. to 29° C.

*Time to produce a rooted young plant, winter.*—About six weeks at 18° C. to 26° C.

*Root description.*—Fleshy, medium in thickness; white in color.

*Rooting habit.*—Freely branching; moderately dense.

Plant description:

*Plant foil growth habit.*—Upright and columnar plant habit; freely basal branching habit with numerous lateral branches; terminal and axillary inflorescences potentially developing at every node and are held upright on strong peduncles; moderately vigorous growth habit.

*Plant height.*—About 33 cm.

*Plant diameter or spread.*—About 38 cm.

*Basal branches.*—Length: About 29 cm. Diameter: About 7 mm. Internode length: About 2.5 cm. Aspect: Mostly upright to slightly outwardly. Strength: Strong. Texture: Longitudinally ridged; pubescent. Color: Close to 187A.

Foliage description:

*Arrangement.*—Alternate, simple.

*Length.*—About 11.25 cm.

*Width.*—About 4 cm.

*Shape.*—Narrowly elliptical to lanceolate.

*Apex.*—Elongate acute.

*Base.*—Attenuate.

*Margin.*—Serrate.

*Texture, upper and lower surfaces.*—Pubescent; rough.

*Venation pattern.*—Pinnate; reticulate.

*Color.*—Developing and fully expanded leaves, upper surface: Close to 147A; venation, close to 147B. Developing and fully expanded leaves, lower surface: Close to 147B; lateral veins, close to 147B; midvein, close to 147C.

*Petiole.*—Length: About 4.5 cm. Diameter: About 5 mm. Texture, upper and lower surfaces: Pubescent. Color, upper and lower surfaces: Centers, close to 147C; towards the margins, close to 147A.

Inflorescence description:

*Appearance.*—Rotate single inflorescence form with ray and disc florets; inflorescences terminal or axillary; inflorescences potentially developing at every node with about one to two open inflorescences per lateral branch at one time; inflorescences held upright on strong peduncles.

*Fragrance.*—Moderate; sweet, pleasant.

*Time to flower.*—Plants flower continuously from the spring throughout the summer in Georgia.

*Inflorescence longevity.*—Depending on temperature, inflorescences maintain good substance for about two to four weeks on the plant; as a cut flower, inflorescences maintain good substance for about two weeks; inflorescences persistent.

*Inflorescence bud.*—Height: About 1.3 cm. Diameter: About 1.4 cm. Shape: Ovoid. Color: Close to 147A.

*Inflorescence size.*—Diameter: About 7 cm. Depth (height): About 2.8 cm. Disc diameter: About 3 cm. Receptacle height: About 1.5 cm. Receptacle diameter: About 7 mm. Receptacle shape: Conical. Receptacle color: Close to NN155D.

*Ray florets.*—Length: About 3.1 cm. Width: About 8 mm. Shape: Lanceolate. Apex: Acute or praemorse. Base: Attenuate; fused into a short corolla tube. Texture, upper and lower surfaces: Smooth, glabrous; satiny. Number of ray florets per inflorescence: About 24 arranged in a single whorl. Aspect: Initially upright to horizontal; flat. Color: When opening, upper surface: Close to 47A. When opening, lower surface: Close to 58A. Fully opened, upper surface: Close to 58B; color becoming closer to 68B with development. Fully opened, lower surface: Close to 58A; color becoming closer to 68B with development.

*Disc florets.*—Shape: Tubular; apex five-pointed. Length: About 1 cm. Diameter: About 2 mm. Number of disc florets per inflorescence: Numerous. Texture: Smooth, glabrous. Color: Apex: Close to 187A. Mid-section: Close to 144A. Base: Close to NN155C.

*Receptacle spines.*—Quantity: One per disc floret. Length: About 1.3 cm. Width: About 1 mm. Shape: Lanceolate to acicular. Apex: Sharply acute. Base: Tapering. Texture: Smooth, glabrous. Color: Apex: Close to 187A. Mid-section: Close to 144A. Base: Close to NN155D.

*Phyllaries.*—Quantity per inflorescence: About 60 in about three to four whorls. Length: About 1.1 cm. Width: About 3 mm. Shape: Lanceolate. Apex: Acute. Base: Truncate. Margin: Entire. Texture, upper and lower surfaces: Pubescent. Color, upper and lower surfaces: Close to 147A.

*Peduncles.*—Length, terminal peduncle: About 6.3 cm. Length, uppermost axillary peduncle: About 4.2 cm. Diameter: About 4 mm. Angle, terminal peduncles:

Erect. Angle, axillary peduncles: About 20° to 30° from vertical. Strength: Strong. Texture: Pubescent; rough. Color: Close to 187A.

*Reproductive organs.*—Androecium: Stamens per disc floret: One. Filament length: About 6 mm. Filament color: Close to 145D. Anther shape: Oblong. Anther length: Less than 1 mm. Anther color: Close to 146C. Pollen amount: Scarce. Pollen color: Close to 17A and 21A. Gynoecium: Pistil length: About 8 mm. Stigma shape: Bi-parted; reflexed. Stigma color: Close to 187A. Style length: About 7 mm. Style color: Close to 150D. Ovary color: Close to 157A. Seeds/fruits: Seed and fruit development have not been observed on plants of the new *Echinacea.*

Disease/pest resistance: Plants of the new *Echinacea* have not been shown to be resistant to pathogens and pests common to *Echinacea.*

Garden performance: Plants of the new *Echinacea* have been observed to have good garden performance and to tolerate rain, wind and temperatures ranging from about −16° C. to about 37° C.

It is claimed:

1. A new and distinct *Echinacea* plant named 'Solar Flare' as illustrated and described.

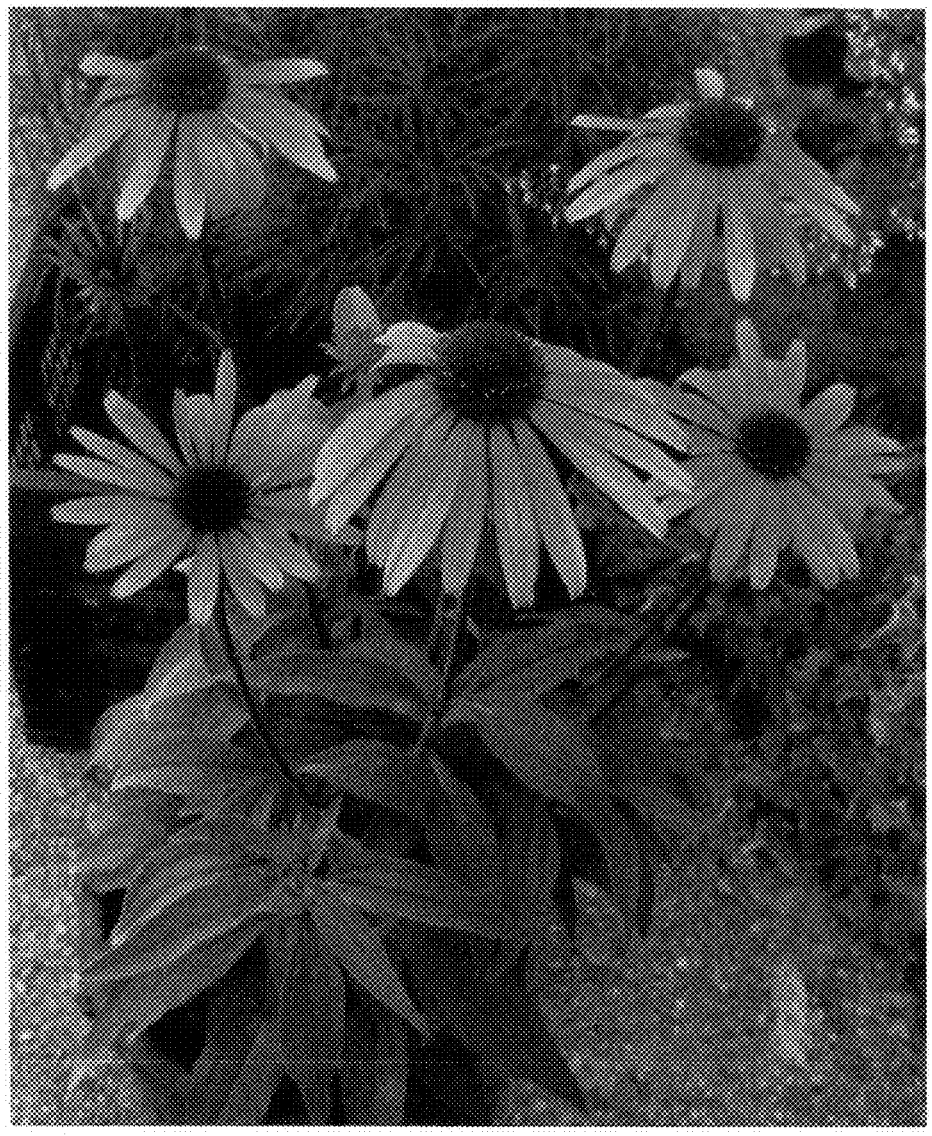

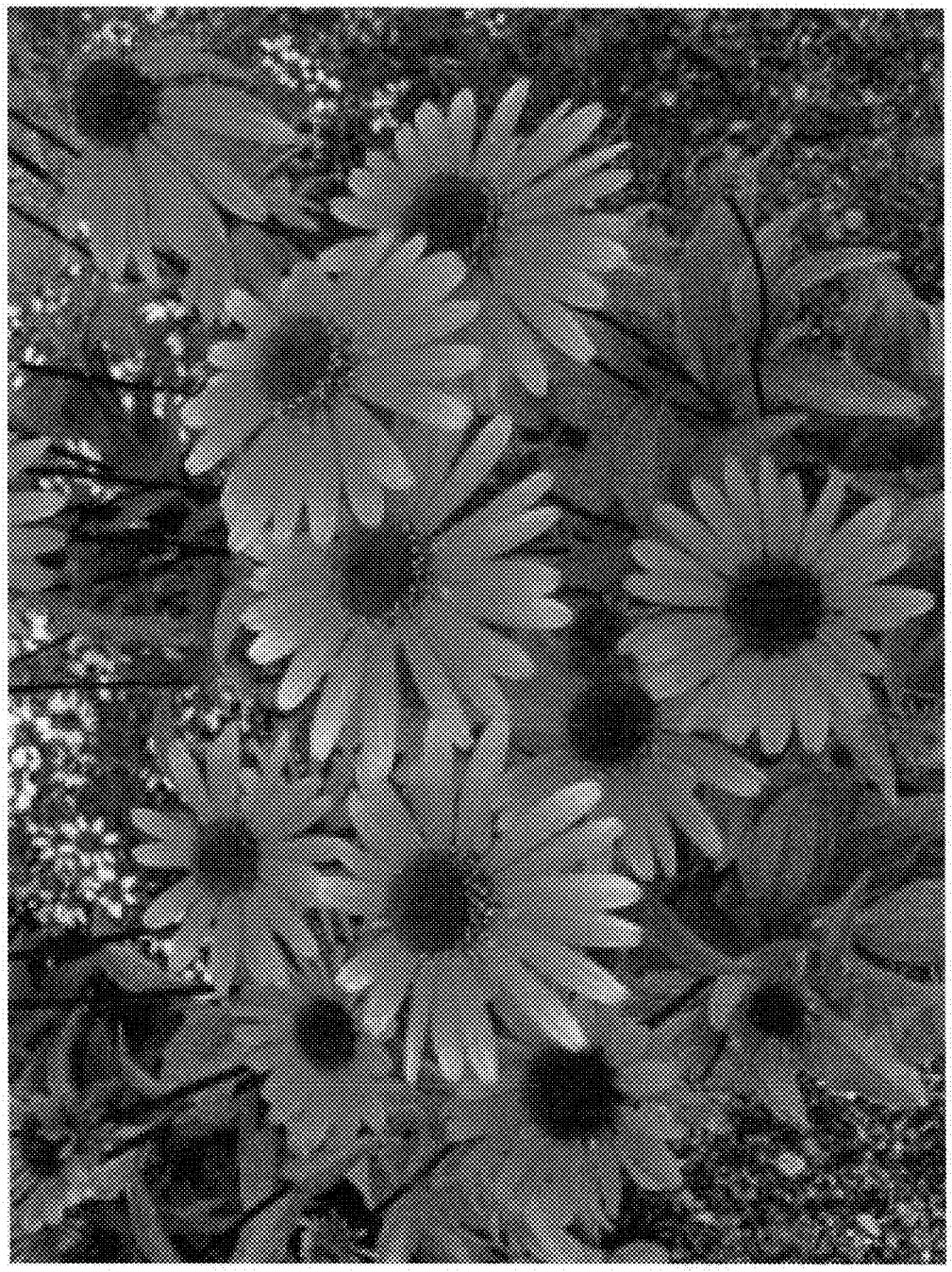

* * * * *